US012797531B2

(12) United States Patent
Fujita et al.

(10) Patent No.: US 12,797,531 B2
(45) Date of Patent: Nov. 17, 2026

(54) TREATMENT MATERIAL

(71) Applicants: KANEKA CORPORATION, Osaka (JP); Broad Bean Science Co., LTD., Shimotsuke (JP)

(72) Inventors: Yuta Fujita, Settsu (JP); Makoto Kuroo, Shimotsuke (JP)

(73) Assignees: KANEKA CORPORATION, Osaka (JP); BROAD BEAN SCIENCE CO., LTD., Shimotsuke (JP)

( * ) Notice: Subject to any disclaimer, the term of this patent is extended or adjusted under 35 U.S.C. 154(b) by 435 days.

(21) Appl. No.: 18/561,569

(22) PCT Filed: Apr. 12, 2022

(86) PCT No.: PCT/JP2022/017596

§ 371 (c)(1),
(2) Date: Nov. 16, 2023

(87) PCT Pub. No.: WO2022/244551

PCT Pub. Date: Nov. 24, 2022

(65) Prior Publication Data

US 2024/0226403 A1 Jul. 11, 2024

(30) Foreign Application Priority Data

May 20, 2021 (JP) ................................ 2021-085358

(51) Int. Cl.
*A61M 1/36* (2006.01)

(52) U.S. Cl.
CPC ........ *A61M 1/3633* (2013.01); *A61M 1/3679* (2013.01); *A61M 2202/0413* (2013.01)

(58) Field of Classification Search
CPC .............................. A61M 1/14; A61M 1/3679
See application file for complete search history.

(56) References Cited

U.S. PATENT DOCUMENTS

2020/0238253 A1* 7/2020 Yonezawa ................ B01J 39/19
2024/0241140 A1* 7/2024 Kuroo .................. G01N 33/493

FOREIGN PATENT DOCUMENTS

WO WO 2018/025809 A1 2/2018

OTHER PUBLICATIONS

Chen et al., "Patients with advanced chronic kidney disease and vascular calcification have a large hydrodynamic radius of secondary calciprotein particles", Nephrol Dial Transplant, 2019, vol. 34, p. 992-1000.

(Continued)

*Primary Examiner* — Leslie R Deak
(74) *Attorney, Agent, or Firm* — Birch, Stewart, Kolasch & Birch, LLP

(57) ABSTRACT

The objective of the present invention is to provide a treatment material for the treatment of a disease of which symptom is alleviated or treated by reducing a blood phosphorus concentration. The treatment material according to the present invention is characterized in comprising a water-insoluble carrier and 1 or more adsorbing groups selected from the group consisting of a phosphate group, a phosphonate group, a phosphinate group, an amino group, a carboxy group and a thiol group, wherein the adsorbing group binds to the water-insoluble carrier through a linker group, the treatment material is used for treating a disease, wherein a symptom of the disease is alleviated or treated by reducing a blood phosphorus concentration, and dialyzed blood is passed through the treatment material to adsorb a calciprotein particle in the dialyzed blood on the adsorbing group, or blood is passed through the treatment material and then dialyzed.

20 Claims, 3 Drawing Sheets

(56) References Cited

OTHER PUBLICATIONS

International Search Report, issued in PCT/JP2022/017596, PCT/ISA/210, dated May 31, 2022.
Makoto Kuro-o, "Klotho and endocrine fibroblast growth factors: marker of chronic kidney disease progression and cardiovascular complications?", Nephrol Dial Transplant, 2018, p. 1-7.
Makoto Kuro-o, "Why is phosphate overload harmful?", Clinical Calcium, 2014, vol. 24, No. 12, total 10 pages.
Miura et al., "Identification and quantification of plasma calciprotein particles with distinct physical properties in patients with chronic kidney disease", Scientific Reports, 2018, vol. 8, No. 1256, p. 1-16.

* cited by examiner

[Fig. 1]
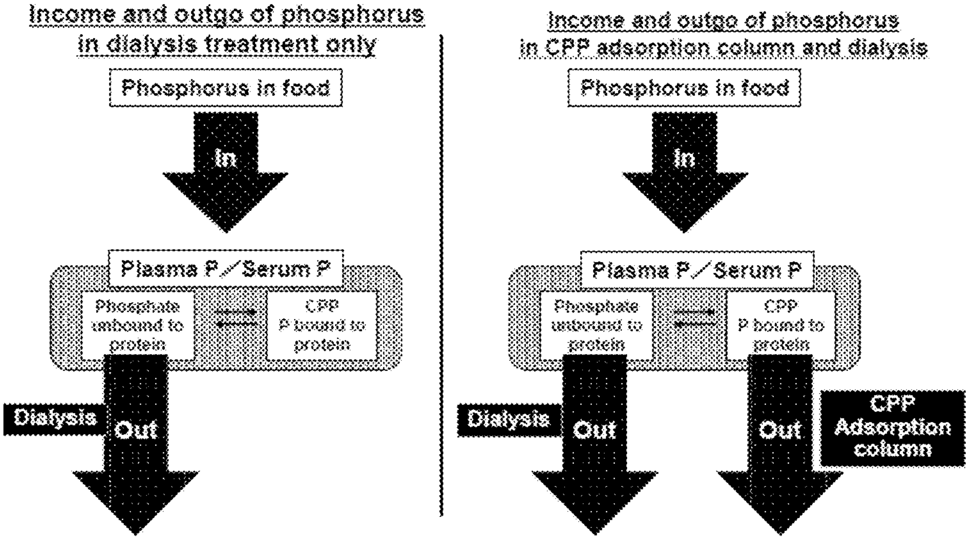
[Fig. 2]
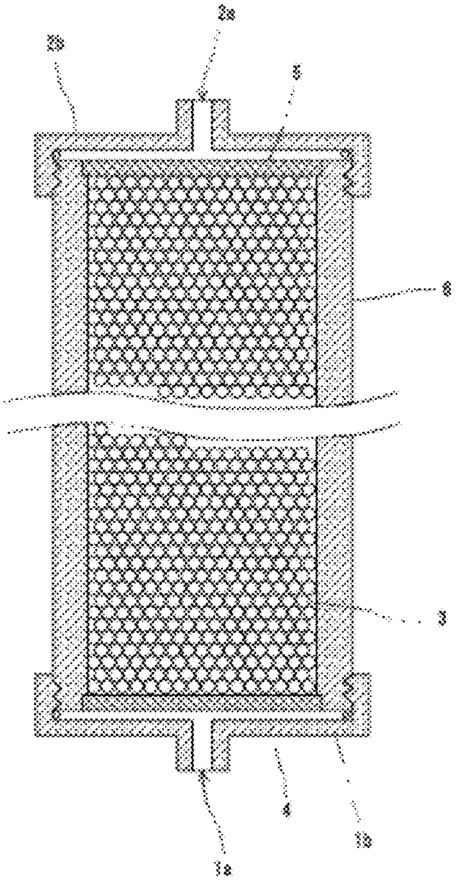

[Fig. 3]
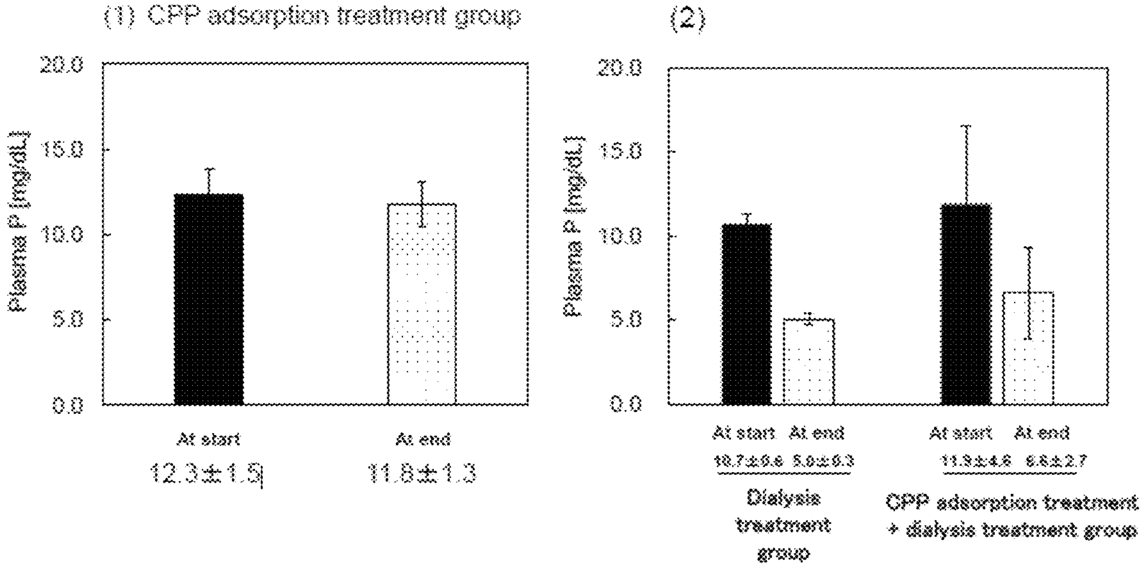
[Fig. 4]
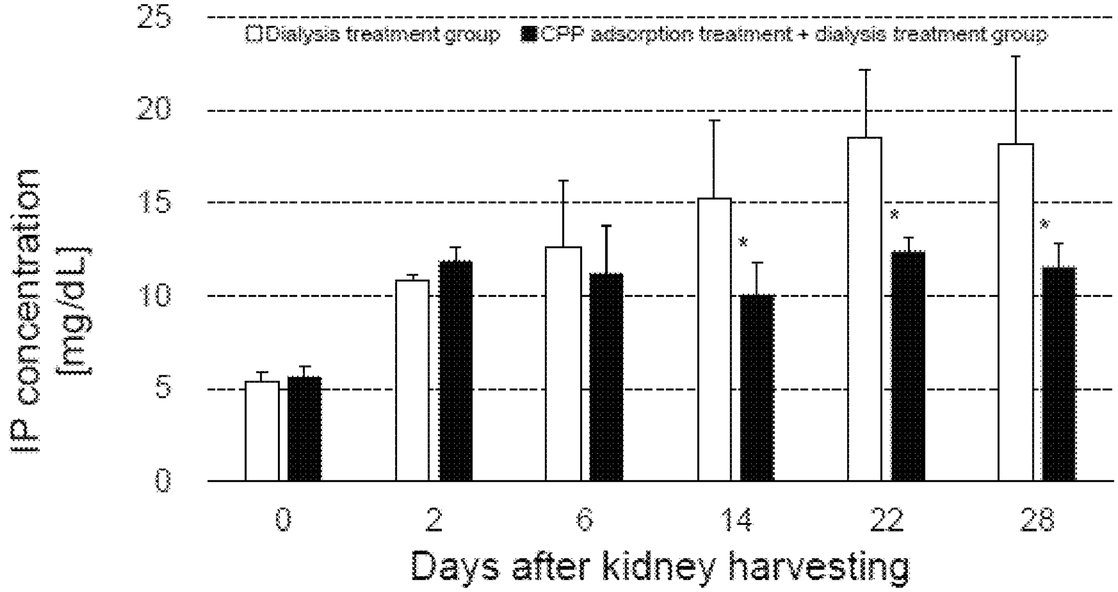

[Fig. 5]
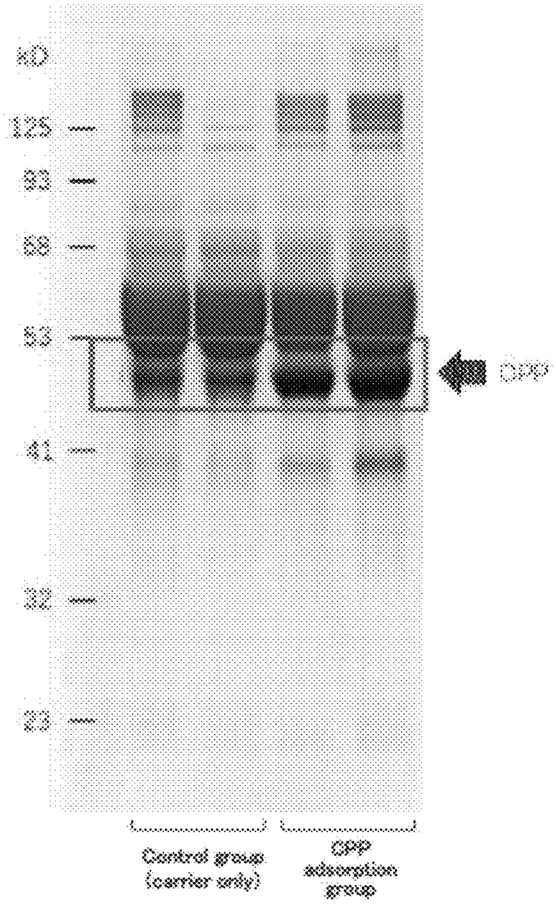

TREATMENT MATERIAL

TECHNICAL FIELD

The present invention relates to a treatment material used for treating a disease of which symptom is relieved or treated by reducing a blood phosphorus concentration.

BACKGROUND ART

Phosphorus is a mineral necessary for the human body, and 85% of phosphorus is present in bones and teeth as calcium phosphate and magnesium phosphate. The remaining 15% is bound to proteins and lipids, is present in cells as a component of cell membranes and nucleic acids, and is also a component of ATP, which generates energy. In addition, phosphorus is involved in various functions in the body. For example, phosphorus works to maintain the pH balance and osmotic pressure of cells.

Excess phosphate is excreted through the kidney into urine, and a patient with renal failure has hyperphosphatemia. Most hyperphosphatemic patients are associated with no symptoms, but calcium deficiency caused by forming an insoluble salt of phosphate with calcium may produce a symptom of hypocalcemia in some cases. In addition, it has also been known that phosphate itself may cause disorder.

For example, the Klotho gene has been identified as a gene involved in premature aging, and it is known that the balance between phosphorus intake and phosphorus excretion is disrupted in a Klotho gene-deficient mouse, resulting in growth impairment and cardiomegaly and premature death by the intake of phosphorus, while a low phosphorus diet reduces premature aging.

Phosphate in blood forms an insoluble salt with calcium as described above, and the insoluble salt is deposited on a cartilage tissue of the joint to cause gout. Serum protein Fetuin-A is known to inhibit calcium deposition by adsorbing calcium phosphate, thereby protecting against vascular calcification. On the one hand, calciprotein particle (CPP), which is a complex of Fetuin-A and calcium phosphate, may aggregate and crystallize the adsorbed amorphous calcium phosphate. Various theories have been proposed in terms of the cause of arteriosclerosis. For example, there is a theory that aggregated CPP advances arteriosclerosis and causes vascular calcification. It is however known that CPP cannot be removed by dialysis (Non-Patent Document 1 to 3).

Accordingly, the inventors of the present invention have developed an adsorbent material to remove CPP from the blood (Patent Document 1).

PRIOR ART DOCUMENT

Patent Document

Patent document 1: WO 2018/025809

Non-Patent Document

Non-patent document 1: Clin. Calcium, 2014 (24), 1785-92
Non-patent document 2: Nephrol. Dial. Transplant., 2018, 1-7
Non-patent document 3: Scientific Reports, 2018, 8, 1256

DISCLOSURE OF THE INVENTION

Problems to be Solved by the Invention

As mentioned above, an adsorbent material to adsorb calciprotein particles has been developed.

However, the inventors found that an adsorbent for adsorbing calciprotein particles can hardly reduce a blood phosphorus concentration in some cases, and that dialysis may not also sufficiently reduce a blood phosphorus concentration. For more detail, a blood phosphorus concentration can be actually reduced by single time dialysis; but even if dialysis is continuously repeated, a blood phosphorus concentration continues to rise after the dialysis.

Thus, the objective of the present invention is to provide a treatment material for the treatment of a disease of which symptom is alleviated or treated by reducing a blood phosphorus concentration.

Means for Solving the Problems

The inventors of the present invention repeated intensive studies in order to solve the above-described problems. As a result, the inventors completed the present invention by finding that a blood phosphorus concentration can be effectively reduced by a combination of a dialysis treatment and the blood treatment using the specific calciprotein particle adsorbent material, and thus a disease of which symptom is alleviated or treated by reducing a blood phosphorus concentration can be treated.

The present invention relates to a treatment material used for the treatment of a disease of which symptom is alleviated or treated by reducing a blood phosphorus concentration.

The present invention is hereinafter described.

[1] A treatment material,
  comprising a water-insoluble carrier and 1 or more adsorbing groups selected from the group consisting of a phosphate group, a phosphonate group, a phosphinate group, an amino group, a carboxy group and a thiol group,
  wherein the adsorbing group binds to the water-insoluble carrier through a linker group,
  the treatment material is used for treating a disease, wherein a symptom of the disease is alleviated or treated by reducing a blood phosphorus concentration, and
  dialyzed blood is passed through the treatment material to adsorb a calciprotein particle in the dialyzed blood on the adsorbing group, or blood is passed through the treatment material and then dialyzed.

[2] The treatment material according to the above [1], wherein the disease is 1 or 2 or more diseases selected from cardiomegaly, sarcopenia, lung emphysema, thymic atrophy, adipose tissue atrophy, dementia, frailty, growth impairment, dermal pruritus, cardiac valvular disease, secondary hyperparathyroidism, abnormal bone metabolism and calciphylaxis.

[3] The treatment material according to the above [1] or [2], wherein the treatment material is further used for suppressing 2 or more diseases selected from cardiac arrest, cerebrovascular accident, pneumonia and digestive disorder.

[4] The treatment material according to any one of the above [1] to [3],
wherein the linker group is a $C_{1-6}$ alkane-diyl group, an ether group, a thioether group, an amino group, a carbonyl group, a thionyl group, an ester group, an amide group, a urea group, a thiourea group, a polyalkylene glycol group, a polyvinyl alcohol group, or a group formed by binding 2 or more and 5 or less of the groups, and
the groups optionally have a substituent group.

[5] The treatment material according to the above [1] to [4], wherein 2 or more phosphonate groups bind to the linker group.

[6] The treatment material according to the above [1] to [5], wherein the water-insoluble carrier is porous.

[7] The treatment material according to the above [6], wherein an exclusion limit molecular weight of the water-insoluble carrier is 1,000 or more and 10,000,000 or less.

[8] Use of a treatment material for treating a disease,
wherein a symptom of the disease is alleviated or treated by reducing a blood phosphorus concentration,
the treatment material comprises a water-insoluble carrier and 1 or more adsorbing groups selected from the group consisting of a phosphate group, a phosphonate group, a phosphinate group, an amino group, a carboxy group and a thiol group,
the adsorbing group binds to the water-insoluble carrier through a linker group, and
dialyzed blood is passed through the treatment material to adsorb a calciprotein particle in the dialyzed blood on the adsorbing group, or blood is passed through the treatment material and then dialyzed.

[9] The use according to the above [8], wherein the disease is 1 or 2 or more diseases selected from cardiomegaly, sarcopenia, lung emphysema, thymic atrophy, adipose tissue atrophy, dementia, frailty, growth impairment, dermal pruritus, cardiac valvular disease, secondary hyperparathyroidism, abnormal bone metabolism and calciphylaxis.

[10] The use according to the above [8] or [9], wherein the linker group is a $C_{1-6}$ alkane-diyl group, an ether group, a thioether group, an amino group, a carbonyl group, a thionyl group, an ester group, an amide group, a urea group, a thiourea group, a polyalkylene glycol group, a polyvinyl alcohol group, or a group formed by binding 2 or more and 5 or less of the groups, and
the groups optionally have a substituent group.

[11] The use according to any one of the above [8] to [10], wherein the treatment material is further used for suppressing 1 or 2 or more diseases selected from cardiac arrest, cerebrovascular accident, pneumonia and digestive disorder.

[12] The use according to any one of the above [8] to [11], wherein 2 or more phosphonate groups bind to the linker group.

[13] The use according to any one of the above [8] to [12], wherein the water-insoluble carrier is porous.

[14] The use according to the above [13], wherein an exclusion limit molecular weight of the water-insoluble carrier is 1,000 or more and 10,000,000 or less.

[15] A method for treating a disease,
comprising the steps of treating blood with a treatment material and subjecting blood to a dialysis treatment,
wherein a symptom of the disease is alleviated or treated by reducing a blood phosphorus concentration,
the treatment material comprises a water-insoluble carrier and 1 or more adsorbing groups selected from the group consisting of a phosphate group, a phosphonate group, a phosphinate group, an amino group, a carboxy group and a thiol group, and
the adsorbing group binds to the water-insoluble carrier through a linker group.

[16] The method according to the above [15], wherein the disease is cardiomegaly, sarcopenia, lung emphysema, thymic atrophy, adipose tissue atrophy, dementia, frailty, growth impairment, dermal pruritus, cardiac valvular disease, secondary hyperparathyroidism, abnormal bone metabolism or calciphylaxis.

[17] The method according to the above [16], wherein 1 or 2 or more diseases selected from cardiac arrest, cerebrovascular accident, pneumonia and digestive disorder are further suppressed.

[18] The method according to the above [15], wherein
the linker group is a $C_{1-6}$ alkane-diyl group, an ether group, a thioether group, an amino group, a carbonyl group, a thionyl group, an ester group, an amide group, a urea group, a thiourea group, a polyalkylene glycol group, a polyvinyl alcohol group, or a group formed by binding 2 or more and 5 or less of the groups, and
the groups may have a substituent group.

[19] The method according to the above [15], wherein 2 or more phosphonate groups are covalently bound to the linker group.

[20] The method according to the above [15], wherein the water-insoluble carrier is porous.

[21] The method according to the above [20], wherein an exclusion limit molecular weight of the water-insoluble carrier is 1,000 or more and 10,000,000 or less.

[22] Use of a treatment material for producing a treatment means to treat a disease,
wherein a symptom of the disease is alleviated or treated by reducing a blood phosphorus concentration,
the treatment material comprises a water-insoluble carrier and 1 or more adsorbing groups selected from the group consisting of a phosphate group, a phosphonate group, a phosphinate group, an amino group, a carboxy group and a thiol group,
the adsorbing group binds to the water-insoluble carrier through a linker group, and
dialyzed blood is passed through the treatment material to adsorb a calciprotein particle in the dialyzed blood on the adsorbing group, or blood is passed through the treatment material and then dialyzed.

[23] The use according to the above [22], wherein the disease is 1 or 2 or more diseases selected from cardiomegaly, sarcopenia, lung emphysema, thymic atrophy, adipose tissue atrophy, dementia, frailty, growth impairment, dermal pruritus, cardiac valvular disease, secondary hyperparathyroidism, abnormal bone metabolism and calciphylaxis.

[24] The use according to the above [22] or [23], wherein the linker group is a $C_{1-6}$ alkane-diyl group, an ether group, a thioether group, an amino group, a carbonyl group, a thionyl group, an ester group, an amide group, a urea group, a thiourea group, a polyalkylene glycol group, a polyvinyl alcohol group, or a group formed by binding 2 or more and 5 or less of the groups, and the groups optionally have a substituent group.

[25] The use according to any one of the above [22] to [24], wherein the treatment material is further used for suppressing 1 or 2 or more diseases selected from cardiac arrest, cerebrovascular accident, pneumonia and digestive disorder.

[26] The use according to any one of the above [22] to [25], wherein 2 or more phosphonate groups bind to the linker group.

[27] The use according to any one of the above [22] to [26], wherein the water-insoluble carrier is porous.

[28] The use according to the above [27], wherein an exclusion limit molecular weight of the water-insoluble carrier is 1,000 or more and 10,000,000 or less.

Effect of the Invention

The present invention can effectively reduce a blood phosphorus concentration and relieve a symptom of a disease of which symptom can be alleviated or treated by reducing a blood phosphorus concentration. Thus, the invention is very useful as a means of treating such a disease.

BRIEF DESCRIPTION OF THE DRAWINGS

FIG. 1 is a figure to schematically show the income and outgo of phosphorus in the cases of dialysis only and the combination of adsorption by CPP and dialysis.

FIG. 2 is a schematic diagram to show an example of an adsorbent vessel using the treatment material of the present invention.

FIG. 3(1) is a graph to show plasma phosphorus concentrations before and after CPP adsorption treatment, and FIG. 3(2) is a graph to show plasma phosphorus concentrations before and after dialysis treatment and CPP adsorption treatment+dialysis treatment.

FIG. 4 is a graph to show changes over time of plasma phosphorus concentrations in the dialysis treatment group and CPP adsorption treatment+dialysis treatment group.

FIG. 5 is a photograph of a gel to show the analysis result of proteins adsorbed on the adsorbent.

MODE FOR CARRYING OUT THE INVENTION

The treatment material of the present invention comprises a water-insoluble carrier and 1 or more adsorbing groups selected from the group consisting of a phosphate group, a phosphonate group, a phosphinate group, an amino group, a carboxy group and a thiol group, wherein the adsorbing group binds to the water-insoluble carrier through a linker group and can adsorb a calciprotein particle. A calciprotein particle is hereinafter abbreviated as "CPP".

CPP is a complex of calcium phosphate and a protein, and more specifically, a complex of calcium phosphate, especially Posner cluster ($Ca_9(PO_4)_6$), and Fetuin-A or the like. CPP is preferably a nano particle formed by polymerizing Fetuin-A or the like containing calcium phosphate. An example of the calcium phosphate includes monetite ($CaHPO_4$), brushite ($CaHPO_4$-$2H_2O$), amorphous calcium phosphate ($Ca_9PO_4)_6$), and hydroxyapatite ($Ca_{10}(PO_4)_6(OH)_2$). A protein in the body fluid other than Fetuin-A may be also incorporated in the complex of CPP in some cases. An example of the protein that is incorporated in the complex other than Fetuin-A includes albumin, fibrinogen, RANKL (Receptor activator of nuclear factor kappa-B ligand), BMP-2 (Bone morphogenetic protein 2), BMP-7 (Bone morphogenetic protein 7), and Osteoprotegerin. CPP may also have an abnormal form that is produced by mutation in a gene and other factors.

CPP binds to an electron-donating group. An example of the electron-donating group includes one or more adsorbing groups selected from the group consisting of a phosphate group (—O—P(=O)(OH)$_2$), a phosphonate group (—P(=O)(OH)$_2$), a phosphinate group (—P(=O)(H)(OH)), an amino group (—$NH_2$), a carboxy group (—$CO_2H$) and a thiol group (—SH). The electron-donating group is preferably 1 or more adsorbing groups selected from the group consisting of a phosphate group, a phosphonate group and a phosphinate group, and more preferably a phosphonate group. The adsorbing group may be partially or wholly in the form of a salt. An example of the counter cation to form such a salt includes an alkali metal ion such as sodium ion and potassium ion; and a Group II metal ion such as calcium ion and magnesium ion. The amino group may be substituted as long as the nucleophilicity thereof is not lost. An example of such a substituent group includes a $C_{1-6}$ alkyl group. The substituent group is preferably a $C_{1-4}$ alkyl group, more preferably a $C_{1-2}$ alkyl group, and even more preferably methyl.

The treatment material of the present invention has a water-insoluble carrier and an adsorbing group for CPP, and the adsorbing group is bound to the water-insoluble carrier through a linker group. The linker group increases the positional freedom degree of the adsorbing group, and thus it becomes easier to adsorb CPP on the adsorbing group. In addition, it is also becomes easier by the linker group to bind the adsorbing group to the water-insoluble carrier.

An example of the linker group includes a $C_{1-6}$ hydrocarbon group, an ether group (—O—), a thioether group (—S—), an amino group (—NH—), a carbonyl group (—C(=O)—), a thionyl group (—C(=S)—), an ester group (—O—C(=O)— or —C(=O)—O—), an amide group (—NH—C(=O)— or —C(=O)—NH—), a urea group (—NH—C(=O)—NH—), a thiourea group (—NH—C(=S)—NH—), a polyalkylene glycol group, a polyvinyl alcohol group, or groups formed by binding 2 or more or 5 or less of the groups. The linker group is preferably a $C_{1-6}$ hydrocarbon group having an ether group, a thioether group, an amino group, a carbonyl group, a thionyl group, an ester group, an amide group, a urea group and/or a thiourea group at one end or both ends thereof, and more preferably a $C_{1-6}$ hydrocarbon group having an ether group, an amino group, a carbonyl group, an ester group and/or an amide group at one end thereof on the water-insoluble carrier side. When the number of the adsorbing groups per the linker group is "n", the valence of the linker group is "n+1", since the linker group binds the water-insoluble carrier to the adsorbing group. For example, when the number of the adsorbing groups per the linker group is 2, the valence of the linker group is 3 for binding the water-insoluble carrier to 2 of the adsorbing groups.

The linker group may have a substituent group. An example of the substituent group includes 1 or more substituent groups selected from a hydroxyl group, a $C_{1-6}$ alkoxy group, an amino group (—$NH_2$) and a halogeno group. The substituent group is preferably a hydroxyl group. The number of the substituent group per the linker group is not particularly restricted as long as the substitution is possible, and for example, is 1 or more and 5 or less, preferably 4 or less or 3 or less, more preferably 2 or less, and even more preferably 1. When the number of the substituent group per the linker group is 2 or more, the substituent groups may be the same as or different from each other.

An example of the $C_{1-6}$ hydrocarbon group includes a $C_{1-6}$ alkane-(n+1)yl group wherein "n" is the number of the adsorbing group per the linker group. The carbon number of the $C_{1-6}$ hydrocarbon group is preferably 2 or more and preferably 5 or less of 4 or less. The $C_{1-6}$ hydrocarbon group may be linear or branched and preferably linear.

The $C_{1-6}$ alkoxy group means a linear or branched saturated aliphatic hydrocarbon oxy group having a carbon number of 1 or more and 6 or less. An example of the $C_{1-6}$ alkoxy group includes methoxy, ethoxy, n-propoxy, isopropoxy, n-butoxy, isobutoxy, t-butoxy, n-pentoxy and n-hexoxy. The $C_{1-6}$ alkoxy group is preferably a $C_{1-4}$ alkoxy group, more preferably a $C_{1-2}$ alkoxy group, and even more preferably methoxy.

An example of the halogeno group includes fluoro, chloro, bromo and iodo. The halogeno group is preferably chloro or bromo and more preferably chloro.

The number of the adsorbing group per the linker group is preferably 2 or more. When 2 or more of the adsorbing groups are closely situated, CPP can be adsorbed more effectively. On the one hand, when the number of the adsorbing group per the linker group is too many, the adsorbing material may possibly become difficult to produce. Thus, the number is preferably 5 or less, more preferably 4 or less or 3 or less, and even more preferably 2.

An example of a compound to constitute the combination of the linker group and the adsorbing group to be bound to the water-insoluble carrier includes pamidronic acid, alendronic acid and neridronic acid.

The term, "water-insoluble", specifically means that when 1 g of the carrier is added into water and the mixture is strongly shaken for 30 seconds every 5 minutes at 20±5° C., the amount of the water required for dissolving the carrier within 30 minutes is 1,000 mL or more and preferably 10,000 mL or more. An example of the water-insoluble carrier includes an inorganic carrier, an organic carrier and a composite carrier produced by the combination thereof, such as an organic carrier-organic carrier and an organic carrier-inorganic carrier. An example of a material of an inorganic carrier includes glass beads and silica gel. An example of a material of an organic carrier includes a synthetic polymer and a polysaccharide. An example of a synthetic polymer includes cross-linked polyvinyl alcohol, cross-linked polyacrylate, cross-linked polyacrylamide and cross-linked polystyrene. An example of a polysaccharide includes crystalline cellulose, cross-linked cellulose, cross-linked agarose and cross-linked dextran. An example of a commercial product includes a porous cellulose gel GCL2000; Sephacryl® S-1000 produced by covalently cross-linking allyl dextran and methylenebisacrylamide; an acrylate carrier Toyopearl®; an agarose cross-linked carrier Sepharose® CL4B; and a cellulose cross-linked carrier Cellufine®. The water-insoluble carrier in the present invention is not restricted to the above exemplified carriers.

The water-insoluble carrier preferably has a large surface area for the purpose of the present invention, and is preferably porous with many pores having an appropriate size. An example of a form of the carrier includes bead, monolith, fiber and membrane such as hollow fiber, and any form can be selected. The inventors found that even when porosity of the water-insoluble carrier is not so high, the treatment material of the present invention can effectively adsorb CPP. Specifically, the exclusion limit molecular weight of the water-insoluble carrier is preferably 1,000 or more and 10,000,000 or less. The exclusion limit molecular weight is more preferably 8,000,000 or less and even more preferably 6,000,000 or less. The inventors found that even when porosity of the water-insoluble carrier is not so high, the treatment material of the present invention can effectively adsorb CPP. Specifically, the exclusion limit molecular weight of the water-insoluble carrier is also preferably 10,000 or more and 50,000 or less, since the water-insoluble carrier having an exclusion limit molecular weight of 30,000 or less is also found to be effective.

The water-insoluble carrier is solid at atmospheric temperature and atmospheric pressure. The size thereof is not particularly restricted and may be appropriately adjusted. For example, the number average particle diameter of the granular water-insoluble carrier may be adjusted to 10 μm or more and 5 mm or less. The average particle diameter is preferably 100 μm or more, more preferably 200 μm or more, and preferably 1 mm or less, more preferably 0.8 mm or less. The average particle diameter of the granular water-insoluble carrier can be measured on the basis of the number by taking a magnified photograph of the carrier using a stereomicroscope or the like and measuring a diameter of the individual carrier.

The water-insoluble carrier generally has many reactive groups such as a hydroxy group on the surface. Thus, for example, a linker compound having the adsorbing group can be bound to the reactive group or a different reactive group bound to the reactive group. For example, an ester bond can be formed by reacting a linker compound having a carboxylic halide group or an active ester group with a hydroxy group on the surface of the water-insoluble carrier. In addition, an ether bond can be formed by reacting a linker compound having a halogeno group with the hydroxy group in the presence of a base. Furthermore, an epoxy group may be added by reacting a halogenohydrin with a hydroxy group on the surface of the water-insoluble carrier to react a linker compound having a nucleophilic group such as a hydroxy group and an amino group (—$NH_2$). A linker compound having an amino group can be bound through the amino group (—NH—) by oxidizing the above-described epoxy group to obtain a formyl group and carrying out a reductive amination reaction with the linker compound. The adsorbing group bound to a linker compound may be protected with an appropriate protective group and deprotected after a binding reaction. Alternatively, a linker group may be bound to the water-insoluble carrier and then the adsorbing group may be bound to the linker group.

The adsorbing group is preferably comprised in the ratio of 10 nmol or more and 100 μmol or less per the unit volume, "1 mL", of the water-insoluble carrier. The ratio is preferably 100 nmol or more, more preferably 1 μmol or more, even more preferably 3 μmol or more, and preferably 50 μmol or less. The volume of the water-insoluble carrier means a sedimentation volume. The sedimentation volume means a volume of the water-insoluble carrier in the case where the water-insoluble carrier is allowed to settle in water while being subjected to vibration, the settling stops, and the volume of the water-insoluble carrier is not further reduced even when vibration is applied. An amount of the adsorbing group per the unit volume of the water-insoluble carrier may be determined by, for example, decomposing the water-insoluble carrier having the adsorbing group under pressurized acidic condition, measuring an amount of the element characteristic to the adsorbing group in the decomposition liquid, and dividing the measured value by a sedimentation volume of the water-insoluble carrier used in the above decomposition, or subtracting an amount of the adsorbing group remaining in the solution after the reaction from an amount of the adsorbing group used for the reaction, and dividing the value by a sedimentation volume of the water-insoluble carrier used for the reaction.

Blood is treated with the treatment material and subjected to dialysis treatment in the present invention. The order of the treatment by the treatment material and the dialysis treatment does not matter. In other words, blood is treated by the treatment material to reduce a CPP amount in the blood and then subjected to dialysis treatment, or blood is subjected to dialysis treatment and then treated by the treatment material to reduce a CPP amount in the blood.

The blood is taken out from a patient using a dialysis device in the present invention. A blood withdrawal rate, i.e., a blood flow rate Qb, may be appropriately adjusted, and may be adjusted to, for example, 50 mL/min or more and 550 mL/min or less in the case of a human.

It is needed that blood is contacted with the treatment material and then the treated blood is separated from the treatment material in order to adsorb CPP in the blood by using the treatment material of the present invention. For example, it is safe, easy and preferred to use an adsorbent vessel prepared by filling a hollow vessel having an inlet and an outlet for the blood with the treatment material. The CPP concentration in the blood can be reduced by contacting the blood with the treatment material of the present invention.

An example of the adsorbent vessel is shown as FIG. 2. The adsorbent vessel of FIG. 2 is prepared by filling the column 6 with the granular treatment material 3. The filters 4 and 5 are attached to both ends of the column 6 to prevent the treatment material 3 from flowing out and to allow blood to pass through the treatment material 3. The lids 1*b* and 2*b* are attached to the column 6's surfaces on which the filters 4 and 5 are placed. The lids can be fixed on the column 6 using clinchers to prevent a liquid from flowing out. Blood can be supplied to the treatment material 3 in the column 6 through the inlet 1*a* formed at the lid 1*b*, and the blood can be discharged through the outlet 2*a* formed at the lid 2*b* after the blood is contacted with the treatment material 3 in the column 6.

CPP is classified into CPP that is a complex of amorphous calcium phosphate and Fetuin-A, and CPP in which at least a part of amorphous calcium phosphate has undergone a phase transition to crystal. The CPP that mainly contains calcium phosphate crystal may be adsorbed on the treatment material of the present invention.

Blood is subjected to dialysis treatment before or after the treatment with the treatment material of the present invention in the present invention. An example of the dialysis treatment includes a general hemodialysis treatment. For example, the dialyzer used for the dialysis treatment may be a hollow fiber-type dialyzer or a parallel-plate (keel-type) dialyzer. The material of the dialysis membrane contained in the dialyzer is not particularly restricted, and polyethylene resin, polystyrene resin, polysulfone resin, polyethersulfone resin, poly(methyl methacrylate) resin, cellulose acetate resin or acrylonitrile-sodium methallylsulfonate copolymer can be used. Also, a dialyzer having a dialysis membrane with large pores, called a high-performance membrane, can be used. The adsorbent vessel comprising the treatment material of the present invention and a dialyzer may be connected to a dialysis device to treat blood. The dialyzer may be connected upstream or downstream of the adsorbent vessel.

The inventors found that even when dialysis is continuously repeated, a blood phosphorus concentration may gradually increase in the long term in some cases though a blood phosphorus concentration can be reduced by single dialysis. The reason may be that phosphorus in blood is the sum of phosphate that is not bound to a protein and a phosphate salt that is bound to a protein as schematically demonstrated in FIG. 1. Specifically, the phosphate that can pass through a dialysis membrane can be removed by dialysis, while CPP having a size larger than the pores of a dialysis membrane cannot be removed by dialysis and remains in the blood even after dialysis. Thus, CPP may be formed from phosphate and a blood phosphorus concentration tends to gradually increase in the long term in the case of dialysis only. In contrast, when blood is subjected to both dialysis treatment and CPP adsorption treatment, phosphorus metabolism in the body may be improved and a blood phosphorus concentration may be reduced in a stable and effective manner by simultaneously removing phosphate and CPP.

A blood phosphorus concentration can be measured by a conventional method. For example, a plasma sample or a serum sample is prepared from a blood sample by centrifugation or the like, and the concentration can be measured by PNP-XDH method or direct molybdate method. In other words, a blood phosphorus concentration specifically means a plasma phosphorus concentration or a serum phosphorus concentration. The PNP-XDH method means a method for measuring an inorganic phosphorus concentration in a sample by producing hypoxanthine from an inorganic phosphate in the sample in the presence of inosine using a function of purine nucleoside phosphorylase (PNP), producing xanthine and reduced nicotinamide adenine dinucleotide (NADH) from the hypoxanthine and oxidized nicotinamide adenine dinucleotide (NAD) using a function of xanthine dehydrogenase (XDH), further producing uric acid and reduced nicotinamide adenine dinucleotide (NADH) from the xanthine and the oxidized nicotinamide adenine dinucleotide (NAD) using a function of xanthine dehydrogenase (XDH), and measuring absorbance at 340 nm, which is the maximum absorption wavelength of NADH. The direct molybdate method means a method for measuring an inorganic phosphorus concentration by combining an inorganic phosphate in the sample with a molybdate salt to produce phosphomolybdic acid and measuring absorbance of ultraviolet region derived from the phosphomolybdic acid.

A treatment frequency of blood by the present invention may be adjusted depending on the symptom, severity, age, gender or the like of a patient. For example, the frequency can be adjusted to 1 time or more and 5 times or less per 1 week for 1 hour or more and 8 hours or less per 1 time.

A blood phosphorus concentration can be effectively reduced by subjecting blood to a dialysis treatment and then passing the blood through the treatment material of the present invention to adsorb CPP in the blood or by passing blood through the treatment material of the present invention to adsorb CPP in the blood and then subjecting the blood to a dialysis treatment. As a result, a disease of which symptom is alleviated or treated by reducing a blood phosphorus concentration can be treated. An example of the disease of which symptom is alleviated or treated by reducing a blood phosphorus concentration includes cardiomegaly, sarcopenia, lung emphysema, thymic atrophy, adipose tissue atrophy, dementia, frailty, growth impairment, dermal pruritus, cardiac valvular disease, secondary hyperparathyroidism, abnormal bone metabolism such as osteoporosis, and calciphylaxis.

A hemodialysis patient may suffer from cardiac arrest, a cerebrovascular accident, pneumonia and a digestive disorder due to a decreased gastric mucosal protective factor and decreased blood flow caused by physical stress, mental stress, a medication and abnormal gastric juice secretion. In particular, cardiac arrest is the leading cause of death among hemodialysis patients in Japan, and a cerebrovascular accident such as cerebral hemorrhage is the third or fourth leading causes of death. An example of a digestive disorder caused by hemodialysis includes gastritis, gastric ulcer and duodenal ulcer. In addition, pneumonia is also suspected to be related to dialysis. Cardiac arrest, a cerebrovascular accident, pneumonia and a digestive disorder caused by hemodialysis can be suppressed by blood treatment using the treatment material of the present invention in addition to hemodialysis. The term "suppression" in this disclosure means that the above-described diseases caused by hemodialysis are prevented, treated and/or a symptom thereof is alleviated.

The treatment material of the present invention can be used for blood treatment, for example, by filling a column included in treatment means such as a hemodialysis device.

The present application claims the benefit of the priority date of Japanese patent application No. 2021-85358 filed on May 20, 2021. All of the contents of the Japanese patent application No. 2021-85358 filed on May 20, 2021, are incorporated by reference herein.

EXAMPLES

Hereinafter, the examples are described to demonstrate the present invention more specifically, but the present invention is in no way restricted by the examples, and the examples can be appropriately modified to be carried out within a range that adapts to the contents of this specification. Such a modified example is also included in the range of the present invention.

Example 1

(1) Preparation of CPP Adsorption Column

An alkaline solution was added to 970 mL of porous cellulose beads (exclusion limit molecular weight: 5,000,000; particle diameter: 400 to 500 μm) to adjust the total volume to 1,494 mL, and then 534 mL of epichlorohydrin was added thereto to be reacted at 40° C. for 2 hours. The beads were sufficiently washed with water after the reaction to obtain epoxidized cellulose beads. A sodium alendronate solution was added to the obtained epoxidized cellulose beads, and the mixture was shaken at 50° C. for 5 hours or more. Then, the beads were sufficiently washed with water to obtain Adsorbent material A: alendronic acid-immobilized cellulose beads. Sulfuric acid and nitric acid were added to the dried Adsorbent material A for acid decomposition under pressure using a microwave decomposition device, and the content amount of P element in the obtained solution was measured by ICP-AES method. The amount of immobilized alendronic acid was 6 μmol/mL by the element analysis result.

A citrate buffer was added to 100 mL of the dried Adsorbent material A, and a column having a volume of 100 mL was filled with the suspension of the Adsorbent material A to prepare a CPP adsorption column.

(2) Preparation of Renal Failure Animal Model

Fifteen mini-pigs of 8 to 12 week-old having a weight of 23.2 to 31.9 kg were arbitrarily divided into three groups: 7 pigs in the dialysis treatment group, 4 pigs in the CPP adsorption treatment group, and 4 pigs in the CPP adsorption treatment+dialysis treatment group.

After the mini-pigs were put under sedation by administering 0.05 mg/kg of atropine sulfate, 0.05 mg/kg of medetomidine hydrochloride and 0.5 mg/kg of midazolam into the muscle at the back of neck, the mini-pigs were anesthetize using an inhalation anesthesia apparatus ("Vigor21 II DX" manufactured by ACOMA Medical Industry) in the condition of mixed gas of $N_2O:O_2$=1:1–0.5 to 1.5% isoflurane and sheared at the head region and the abdominal region while allowing the mini-pigs to breathe in the condition of 10 to 15 mL/kg and 18 to 22 times per minute using an inhalator ("PRO-Vmk II" manufactured by ACOMA Medical Industry). The inside of a catheter for measuring blood pressure ("Medicut LCV-UK kit" manufactured by Covidien Japan, size: 16 G, length: 70 cm) was filled with about 10 unit/mL heparinized saline solution, and the catheter was inserted from right aortic side limb or left aortic side limb to bring the tip part thereof to abdominal aorta. The other tip part was inserted subcutaneously into the midline of the back and exposed to the outside of the body.

Then, the inside of a dialysis catheter ("Blood Access UK Catheter Kit" manufactured by NIPRO, cannula outside diameter: 12 Fr) was filled with about 10 unit/mL heparinized saline solution, and the catheter was inserted into the cervical region. The abdomen was incised, and the kidney was dissected. The ureter, renal vein and renal artery were ligated, and the kidney was isolated. JMS hydrophilic Foley catheter (16 Fr, manufactured by JMS) was inserted into the gastric body and fixed to the stomach by pouch suture. The other tip was taken from the abdominal region and fixed to the skin. Then, the skin was sutured.

(3) Experiment

Renal failure model animals were caged in the measurement gauge, and Blood Access catheter was connected to a personal dialysis device ("NCU-12" and "NCV-10" manufactured by NIPRO).

After awakening, the animals of the dialysis treatment group were subjected to dialysis treatment from 2 days after the surgery to remove the kidney by drawing blood in the flow rate of 150 mL/min and directly circulating the blood into the body for 5 hours every 2 days using a dialyzer ("Hollow Fiber Dialyzer FB-90P @ ECO" manufactured by NIPRO, membrane area: 0.9 $m^2$).

The above-described CPP column was used and the blood was passed through the CPP column in place of the dialyzer in a similar condition described above in the CPP adsorption treatment group.

The CPP adsorption column was washed with 1 L of a saline solution containing 2000 unit/L levaheparin injection solution just before use and installed upstream of the dialyzer, and the blood was passed through the CPP adsorption column and the dialyzer in a similar condition described above in the CPP adsorption treatment+dialysis treatment group.

During the experimental period, 200 g of a high-phosphorus feed (MP 1.2×P special-order feed, manufactured by Oriental Yeast) and 200 g of ordinary solid feed (NS, manufactured by Nisseiken) were mixed and given to the animals at 16:00 to 18:00. The animals were fed after awakening on the operation day for implanting the catheter and after the treatment on the dialysis day. The animals were fasted on the day to harvest the kidney and the day after. The animals were allowed to drink tap water freely using an automatic water supply system.

The plasma phosphorus concentration was measured in the blood drawn from the animals and the treated blood 2 days after the kidney harvesting. Specifically, the blood was collected in a heparin Na-treated vacuum blood collection tube and centrifuged to obtain plasma, and the plasma phosphorus concentration was measured by PNP-XDH method using an automated biochemical analyzer ("AU480" manufactured by Beckman Coulter). Also, the plasma phosphorus concentration was measured in the blood drawn from the animals and the treated blood 6, 14, 22 and 28 days after the kidney harvesting in the dialysis treatment group and the CPP adsorption treatment+dialysis treatment group.

By 30 days after the kidney harvesting operation, 4 out of 7 pigs in the dialysis group and 4 out of 4 pigs in the CPP adsorption treatment+dialysis treatment group survived. The CPP adsorption treatment group was evaluated only after the first treatment 2 days after the kidney harvesting. The cause of the sudden death in the dialysis treatment group was investigated; as a result, the cause was cardiac arrest, and gastric ulcer was also observed. On the one hand, since no pigs in the CPP adsorption treatment+dialysis treatment group died suddenly, cardiac arrest and digestive disorder caused by dialysis treatment may be suppressed by treating the blood using the treatment material of the present invention.

(4) Result

The plasma phosphorus concentrations before and after the CPP adsorption treatment are shown in FIG. 3(1), and the plasma phosphorus concentrations before and after the dialysis treatment and before and after the CPP adsorption treatment+dialysis treatment are shown in FIG. 3(2).

It was demonstrated as shown in FIG. 3 that a dialysis treatment can reduce plasma phosphorus concentration but a CPP adsorption treatment can hardly reduce plasma phosphorus concentration. It was predicted on the basis of FIG. 1 that the equilibrium would be shifted to the right by removing CPP and thus plasma phosphorus concentration would be reduced, but the plasma phosphorus concentration was not reduced by removing CPP only.

The changes over time in plasma phosphorus concentration in the dialysis treatment group and the CPP adsorption treatment+dialysis treatment group are shown in FIG. 4. In FIG. 4, "*" indicates a significant difference at $p<0.05$ by t-test.

The plasma phosphorus concentrations continued to increase over time with the ingestion of the high-phosphate feed by the dialysis treatment only as shown in FIG. 4.

In contrast, when the dialysis treatment was performed in addition to the CPP adsorption treatment, the plasma phosphorus concentration was initially similar to that of the case of the dialysis treatment only but stably tended to be lower and significantly reduced in comparison with the case of the dialysis treatment only, in which the plasma phosphorus concentration kept increasing.

The reason for the above result may be that phosphorus metabolism in the body was improved and the blood phosphorus concentration was reduced in a stable and effective manner by subjecting the blood to both of the dialysis treatment and the CPP adsorption treatment to simultaneously remove the phosphate that is not bound to a protein and the phosphate that is bound to a protein.

It was demonstrated as the above that phosphate in blood can be effectively reduced by the blood treatment using the combination of dialysis and the CPP adsorbent material.

Example 2

(1) Preparation of CPP Adsorption Column

A sodium alendronate solution was added to 530 mL of epoxidized porous cellulose beads (exclusion limit molecular weight: 30,000; particle diameter: 440 to 480 μm), and the mixture was shaken at 70° C. for 5 hours or more. Then, the beads were sufficiently washed with water to obtain alendronic acid-immobilized cellulose beads, i.e. Adsorbent material B. Sulfuric acid and nitric acid were added to the dried Adsorbent material B for acid decomposition under pressure using a microwave decomposition device, and the content amount of P element in the obtained solution was measured by ICP-AES method. The amount of immobilized alendronic acid was 10 μmol/mL by the element analysis result.

The CPP adsorption column was prepared by adding purified water to 100 mL of the above adsorbent material B in a dry state and filling a 100 mL column with the suspension of the Adsorbent material B. A column was filled with epoxied porous cellulose beads on which alendronic acid was not immobilized for comparison.

(2) Experiment

Two renal failure model animals were prepared, and Blood Access catheter was connected to a personal dialysis device ("NCU-12" and "NCV-10" manufactured by NIPRO) similarly to Example 1. The CPP adsorption column and the column filled with the carrier only were washed with 1 L of a saline solution containing 2000 unit/L of levaheparin injection solution just before use and installed in the dialyzer. The blood was drawn in the flow rate of 150 mL/min and directly circulated for 5 hours 2 days after the kidney harvesting operation.

During the experimental period, 200 g of a high-phosphorus feed (MP 1.2×P special-order feed, manufactured by Oriental Yeast) and 200 g of ordinary solid feed (NS, manufactured by Nisseiken) were mixed and given to the animals at 16:00 to 18:00. The animals were fed after awakening on the operation day for implanting the catheter and after the treatment on the dialysis day. The animals were fasted on the day to harvest the kidney and the day after. The animals were allowed to drink tap water freely using an automatic water supply system.

The adsorbent material was taken out from the column using a saline solution after returning the blood and washed with heparin-containing Dulbecco's modified Eagle medium. To the adsorbent material having a mass of 0.10 g in a wet condition, 180 μL of EDTA solution was added to elute the CPP adsorbed on the adsorbent material. The eluent was subjected to polyacrylamide electrophoresis to analyze the protein size. The result is shown in FIG. 5.

The exclusion limit molecular weight of the water-insoluble carrier was 30,000 as shown in FIG. 5. It was confirmed that the water-insoluble carrier having pores that was smaller than CPP could not adsorb CPP but CPP adsorbent material containing the same water-insoluble carrier could adsorb CPP.

In addition, the water-insoluble carrier of Example 2 may reduce a blood phosphorus concentration, since it is demonstrated in Example 1 that the adsorption on CPP had a correlation to the reduction of a blood phosphorus concentration and the water-insoluble carrier of Example 2 could adsorb CPP.

The invention claimed is:

1. A method for treating a patient experiencing symptoms of a first disease caused by hyperphosphatemia, comprising the steps of subjecting blood from a patient to a dialysis treatment and, before or after said dialysis treatment, contacting said blood with a treatment material, whereby a symptom of the first disease is alleviated or treated by reducing the concentration of phosphorus in said blood, wherein said treatment material comprises a water-insoluble carrier having bound thereto a plurality of adsorbing components, each of said adsorbing components comprising a linker and at least one calciprotein-adsorbing group selected from a phosphate group, a phosphonate group, a phosphinate group, an amino group, a carboxy group and a thiol group, and the calciprotein-adsorbing group being bound to the water-insoluble carrier through the linker.

2. The method according to claim 1, wherein said first disease is cardiomegaly, sarcopenia, lung emphysema, thymic atrophy, adipose tissue atrophy, dementia, frailty, growth impairment, dermal pruritus, cardiac valvular disease, secondary hyperparathyroidism, abnormal bone metabolism or calciphylaxis.

3. The method according to claim 2, wherein at least one second disease is also suppressed by said method, wherein said second disease is selected from cardiac arrest, cerebrovascular accident, pneumonia and digestive disorder.

4. The method according to claim 1, wherein the linker comprises a linker group that is at least one member selected from a $C_{1-6}$ hydrocarbon group, an ether group, a thioether group, an amino group, a carbonyl group, a thionyl group, an ester group, an amide group, a urea group, a thiourea group, a polyalkylene glycol group, and a polyvinyl alcohol group.

5. The method according to claim 4, wherein said linker comprises two or more of said linker groups.

6. The method according to claim 4, wherein said linker comprises 1-5 of said linker groups.

7. The method according to claim 4, wherein said linker further comprises at least one substituent group.

8. The method according to claim 1, wherein said adsorbing component comprises 2 or more phosphonate groups covalently bound to the linker.

9. The method according to claim 1, wherein the water-insoluble carrier is porous.

10. The method according to claim 9, wherein said water-insoluble carrier has a molecular weight exclusion limit of 1,000 to 10,000,000.

11. The method according to claim 1, wherein said adsorbent component comprises at least one member selected from pamidronic acid, alendronic acid and neridronic acid.

12. A method for reducing the concentration of phosphorus in the blood of a patient experiencing symptoms caused by hyperphosphatemia, said method comprising the steps of:

(a) subjecting said blood of a patient to a dialysis treatment and, before or after said dialysis treatment, (b) contacting said blood with a treatment material, wherein said treatment material comprises a water-insoluble carrier having bound thereto a plurality of adsorbing components, each of said adsorbing components comprising a linker and at least one calciprotein-adsorbing group selected from a phosphate group, a phosphonate group, a phosphinate group, an amino group, a carboxy group and a thiol group, and the calciprotein-adsorbing group being bound to the water-insoluble carrier through said linker.

13. The method according to claim 12, wherein the linker comprises a linker group that is at least one member selected from a $C_{1-6}$ hydrocarbon group, an ether group, a thioether group, an amino group, a carbonyl group, a thionyl group, an ester group, an amide group, a urea group, a thiourea group, a polyalkylene glycol group, and a polyvinyl alcohol group.

14. The method according to claim 13, wherein said linker comprises two or more of said linker groups.

15. The method according to claim 13, wherein said linker comprises 1-5 of said linker groups.

16. The method according to claim 13, wherein said linker further comprises at least one substituent group.

17. The method according to claim 12, wherein said adsorbing component comprises 2 or more phosphonate groups covalently bound to the linker.

18. The method according to claim 12, wherein the water-insoluble carrier is porous.

19. The method according to claim 18, wherein said water-insoluble carrier has a molecular weight exclusion limit of 1,000 to 10,000,000.

20. The method according to claim 12, wherein said adsorbent component comprises at least one member selected from pamidronic acid, alendronic acid and neridronic acid.

* * * * *